US008962240B2

(12) United States Patent
Limoges et al.

(10) Patent No.: US 8,962,240 B2
(45) Date of Patent: Feb. 24, 2015

(54) METHOD FOR ELECTROCHEMICALLY IDENTIFYING TARGET NUCLEOTIDE SEQUENCES

(75) Inventors: Benoît Limoges, Brétigny-sur-Orge (FR); Thibaut Defever, Orchies (FR); Damien Marchal, Paris (FR)

(73) Assignees: Universite Paris Diderot-Paris 7 (FR); Centre National de la Recherche Scientifique (CNRS) (FR)

( * ) Notice: Subject to any disclaimer, the term of this patent is extended or adjusted under 35 U.S.C. 154(b) by 448 days.

(21) Appl. No.: 12/995,512

(22) PCT Filed: Jun. 4, 2009

(86) PCT No.: PCT/FR2009/000653
§ 371 (c)(1),
(2), (4) Date: Jan. 26, 2011

(87) PCT Pub. No.: WO2009/147322
PCT Pub. Date: Dec. 10, 2009

(65) Prior Publication Data
US 2011/0136126 A1 Jun. 9, 2011

(30) Foreign Application Priority Data
Jun. 5, 2008 (FR) ...................................... 08 03143

(51) Int. Cl.
*C12Q 1/68* (2006.01)

(52) U.S. Cl.
CPC .................................... *C12Q 1/6851* (2013.01)
USPC ........ 435/6.1; 435/287.2; 435/6.11; 435/6.12

(58) Field of Classification Search
None
See application file for complete search history.

(56) References Cited

U.S. PATENT DOCUMENTS

| | | | |
|---|---|---|---|
| 6,063,573 A * | 5/2000 | Kayyem | 435/6.11 |
| 6,824,974 B2 * | 11/2004 | Pisharody et al. | 435/4 |
| 6,833,267 B1 * | 12/2004 | Kayyem | 435/287.1 |
| 7,479,557 B2 * | 1/2009 | Gao et al. | 544/64 |
| 8,313,638 B2 * | 11/2012 | Marchal et al. | 205/793.5 |
| 2004/0197801 A1 * | 10/2004 | Liu et al. | 435/6 |
| 2008/0125333 A1 * | 5/2008 | Labgold et al. | 506/39 |
| 2009/0065372 A1 | 3/2009 | Marchal et al. | |

FOREIGN PATENT DOCUMENTS

| WO | WO 2007/099236 A | 9/2007 | |
|---|---|---|---|
| WO | WO2007099236 | * 9/2007 | C12Q 1/68 |

OTHER PUBLICATIONS

Gorner et al. (Binding of Ru(bpy)3(2+) and Ru(phen)3(2+) to polynucleotides and DNA: effect to added salts on the absorption and luminescence properties, J Photochem Photobiol B. Jul. 1988;2(1):67-89).*
Voltammetry (Jun. 7, 2004; available at http://mail.chiangmai.ac.th/~scijjkmn/voltammetry.htm).*
Ririe et al. (Product Differentiation by Analysis of DNA Melting Curves during the Polymerase Chain Reaction, Analytical Biochemistry 245, 154-160 (1997)).*
Ahmed et al. (Electrochemical DNA biosensor using a disposable electrochemical printed (DEP) chip for the detection of SNPs from unpurified PCR amplicons, Analyst, Mar. 14, 2007, 132, 431-438).*
Kobayashi et al. (Electrochemical DNA quantification based on aggregation induced by Hoechst 33258, Electrochemistry Communications 6 (2004) 337-343).*
Deféver et al. (Real-Time Electrochemical PCR with a DNA Intercalating Redox Probe, Anal. Chem. 2011, 83, 1815-1821, Jan. 31, 2011).*
Yeung et al. (Electrochemistry-Based Real-Time PCR on a Microchip, Anal. Chem. 2008, 80, 363-368).*
Yeung et al. (Electrochemical Real-Time Polymerase Chain Reaction, J. Am. Chem. Soc. 2006, 128, 13374-13375, Published on Web Sep. 23, 2006).*
Masaaki Kobayashi, et al., "Electrochemical DNA quantification based on aggregation induced by Hoechst 33258", *Electrochemistry Communications* 6, (2004) pp. 337-343.
International Search Report dated Oct. 19, 2009, issued in corresponding international application No. PCT/FR2009/000653.
Boon E M et al: "Mutation detection in electrocatalysis at DNA-modified electrodes." Nature Biotechnology Nature Publishing Group, New York, NY, US, vol. 18, No. 10, Oct. 1, 2000, pp. 1096-1100, XP002400609 ISSN: 1087-0156 p. 1096, col. 2, lines 1-3.
Millan K M et al: "Sequence-Selective Biosensor for DNA Based on Electroactive Hybridization Indicators." Analytical Chemistry, American Chemical Society. Columbus, US, vol. 65, Jan. 1, 1993, pp. 2317-2323, XP000396986 ISSN: 0003-2700.

* cited by examiner

*Primary Examiner* — Christopher M Babic
*Assistant Examiner* — Aaron Priest
(74) *Attorney, Agent, or Firm* — Ostrolenk Faber LLP

(57) ABSTRACT

A method and assembly for electrochemically identifying target nucleotide sequences. The method includes supplying a biological sample that may contain a predetermined target nucleotide sequence; supplying activatable amplification materials comprising free nucleotides to form replicated target nucleotide sequences; supplying an oxido-reducible compound capable of being inserted during replication between the nucleotides forming the replicated target sequences; and activating the activatable amplification materials before applying an electric field to the sample in order to activate the oxido-reducible compound. The replicated target sequences cause inhibition of electrochemical activity of the inserted oxido-reducible compound, and the presence of the predetermined target nucleotide sequence is determined in instances where the electric current decreases.

18 Claims, 4 Drawing Sheets

METHOD FOR ELECTROCHEMICALLY IDENTIFYING TARGET NUCLEOTIDE SEQUENCES

CROSS REFERENCE TO RELATED APPLICATIONS

The present application is a 35 U.S.C. §371 National Phase conversion of PCT/FR2009/000653, filed Jun. 4, 2009, which claims benefit of French Application No. 0803143, filed Jun. 5, 2008, the disclosure of which is incorporated herein by reference. The PCT International Application was published in the French language.

BACKGROUND OF THE INVENTION

The present invention relates to a method and to an assembly for electrochemically identifying target nucleotide sequences.

One field of application envisioned is in particular that of the rapid analysis of biological samples that may contain bacteria or viruses, and more generally any nucleic acid.

Known electrochemical detection methods already make it possible to demonstrate target nucleic acid sequences. Some make use of both nucleic acid amplification processes, for example of PCR (polymerase chain reaction) type, and cyclic voltammetry processes. According to one of these methods, a biological sample containing a nucleic acid, which exhibits a predetermined target nucleotide sequence, is provided and an oxidizing agent capable of oxidizing at least one of the nucleotide bases of the target sequence is added to the biological sample. The amplification means comprise nucleotides of a type including the oxidizable nucleotide base and the nucleotides are of course intended to be consumed during the implementation of the amplification process so as to produce replicated nucleic acid sequences. Simultaneously, or after each amplification step, an electric field is applied to the sample so as to bring about reaction of the oxidizing agent with the oxidizable nucleotide base, and the electric current which consequently passes through the sample is measured. According to this method, described more specifically in document PCT/FR2007/000373, the presence of the predetermined target sequence and the initial amount thereof are determined when the electric current decreases over the course of the amplifications. This is because, during the amplification process, the number of free nucleotides of the amplification means decreases since they are incorporated into the synthesized nucleic acids. The oxidizing agent can then react only with an increasingly limited amount of free nucleotides. Consequently, fewer and fewer electron transfers due to the oxidation reaction occur, and the electric current decreases.

Thus, such a method makes it possible to rapidly detect and quantify the presence of a given nucleic acid in any biological sample.

A problem which arises and which the present invention aims to solve is not only that of providing another electrochemical detection method which makes it possible to detect the presence of a target nucleotide sequence in a biological sample, but also that of being able to identify its nature and to quantify it.

SUMMARY OF THE INVENTION

With the aim of solving this problem, according to a first aspect, the present invention proposes a method for electrochemically identifying target nucleotide sequences. Said method is of the type according to which a biological sample that may contain a predetermined target nucleotide sequence is provided, as are activatable amplification means comprising free nucleotides in order to cause the replication of said predetermined target nucleotide sequence and the formation of replicated target nucleotide sequences. According to the method, an oxido-reducible compound capable of reacting with respect to said nucleotides is also provided and said oxido-reducible compound is brought into contact with said biological sample. Said activatable amplification means are then activated and an electric field is applied to said sample in order to activate said oxido-reducible compound and the electric current representative of the electrochemical activity of said oxido-reducible compound, which passes through said sample, is measured. Thus, the presence of said predetermined target nucleotide sequence is determined if the electric current decreases. According to the invention, an oxido-reducible compound capable of intercalating, during the replication, between the nucleotides forming said replicated target sequences is provided, said replicated target sequences causing the inhibition of the electrochemical activity of said intercalated oxido-reducible compound, by virtue of which the electric current decreases.

In addition to the free nucleotides, the activatable amplification means comprise primers which are oligonucleotide acids specific for and complementary to the target nucleotide sequence to be detected, and a polymerase. Moreover, as will be explained in detail hereinafter, the electric field is applied to said sample by bringing electrodes into contact with said sample and by applying a potential difference between these electrodes.

Thus, one feature of the invention is to provide an oxido-reducible compound which will not oxidize the nucleotide bases of the free nucleotides in the sample, as is the case in the abovementioned prior art document, but which will intercalate between the nucleotides forming the replicated target sequences.

Preferably, said activatable amplification means are activated according to successive amplification cycles and, at each amplification cycle, said replicated target sequence is duplicated. The oxido-reducible compound then intercalates between the nucleotides forming said replicated target sequences and loses its oxido-reducible activity with respect to the applied electric field. Consequently, over the course of the amplification cycles, the electrical signal measured decreases.

The number of amplification cycles corresponding to the decrease in the electric current is then advantageously recorded in order to determine the concentration of said target nucleotide sequence in said sample. This is because the decrease in the signal measured is proportional to the amount of replicated target nucleotide sequence. It is possible to deduce from this proportionality the amount of predetermined target nucleotide sequence initially present in said sample. Thus, the activation of said activatable amplification means is thus repeated according to a certain number of amplification cycles, and the number of cycles of said amplification means when the electric current decreases is recorded in order to determine the concentration of said target nucleotide sequence in the sample. Specifically, the more predetermined target nucleotide sequences the biological sample contains, the lower the number of amplification cycles necessary in order for the intensity of the electric current to fall. Conversely, the fewer predetermined target sequences the sample contains, the higher the number of amplification cycles. In that way, as will be explained in greater detail in the rest of the description, this method also makes it possible to quantify the concentration of predetermined target sequence in the biological sample.

It will be specified that the term "oxido-reducible compound" describes not only redox compounds, but also compounds capable of being oxidized under certain conditions, and of being reduced under others.

According to one embodiment of the invention which is particularly advantageous, after the predetermined target nucleotide sequence has been amplified, said sample is also provided with thermal energy in order to cause the release of said intercalated oxido-reducible compound, and an electric field is applied to said sample in order to simultaneously record the variations in electric current which passes through said sample. The amount of thermal energy Q corresponding to the maximum variations in the electric current which are recorded is then determined in order to identify the nature of said predetermined target nucleotide sequence. Advantageously, said sample is supplied with thermal energy in such a way as to cause a gradual increase in the temperature of said sample. Thus, the variations in electric current as a function of the thermal energy provided, or more concretely of the temperature over a given range, are recorded. The nature of said predetermined target nucleotide sequence is identified from the maximum variation in the electric current at a given temperature. This is because, according to the nature of the amplified target sequence, the maximum variation in the electric current at a given temperature is characteristic of said replicated target nucleotide sequence.

Thus, when the sample and, consequently, the replicated target nucleotide sequences, are supplied with sufficient thermal energy, the double strands of the replicated target nucleotide sequences tend to separate into two single strands and to consequently release the intercalated oxido-reducible compound, which then recovers its electrochemical activity. The double strands of the replicated target nucleotide sequences separate from one another for a given thermal agitation, i.e. at a given temperature, such that the release of the oxido-reducible compound, which is then measured by means of the electric current generated at the electrodes, occurs abruptly, in a virtually discrete manner, i.e. over a narrow temperature range, when a given amount of thermal energy is given to the sample.

Advantageously, said sample is supplied with thermal energy in such a way as to cause a gradual increase in the temperature of said sample, for example between 40° C. and 98° C. In this temperature range, the double strands of the replicated target nucleotide sequence will gradually change from a paired state, in which each of the nucleotide bases of the replicated target sequences are associated in a complementary manner, to a dissociated state where each replicated target sequence will end up being single-stranded. The change from a double-stranded state to a single-stranded state therefore takes place within a narrow temperature range, which is characterized by a "dissociation" temperature, generally noted Tm, characteristic of the nature of the replicated target nucleotide sequence.

In addition, the electric current representative of the electrochemical activity of said oxido-reducible compound is preferably measured at a predetermined temperature of said sample, at which no other molecule formed or in the process of being formed inhibits the oxido-reducible compound, for example the primer dimers. Advantageously, said predetermined temperature is noticeably lower than, but nevertheless close to, the temperature of said sample corresponding to the predetermined amount of thermal energy Q, such that, at this high temperature, all the other molecules, which are smaller in size than the replicated target nucleotide sequence, are dehybridized, whereas the replicated target nucleotide sequence remains intact.

In that way, the amount of current resulting from the release of said oxido-reducible compound by the various primer dimers or from any other smaller molecules, that the thermal energy already supplied has made it possible to dissociate, is eliminated from the electric current measured.

Preferably, voltammetry is used to measure and record the electric current or said variations in electric current. This potentiodynamic method consists in applying, between two electrodes, as will be explained in greater detail in the rest of the description, a potential which is variable over time and in concomitantly recording the variation in current which results therefrom. Preferably, square wave voltammetry is used. Other electrochemical techniques are of course potentially applicable, for example differential pulse voltammetry or linear or cyclic scan voltammetry or else sampled current voltammetry or alternating current voltammetry.

According to one embodiment of the invention which is particularly advantageous, said oxido-reducible compound provided is a complex of a transition metal, for example a metal of column VIIIA of Mendeleev's table, and more specifically osmium. In addition, the oxido-reducible compound advantageously has at least one nucleic-acid-sequence-intercalating ligand, and for example a dipyridophenazine ligand, which is capable of intercalating between the paired strands formed by the replicated target nucleotide sequences.

Furthermore, the oxido-reducible compound has at least one bipyridine ligand and advantageously two ligands of this type. A complex of osmium with an accompanying dipyridophenazine ligand and two accompanying bipyridine ligands will be described in greater detail in the rest of the description. Moreover, it will be observed that some entirely organic oxido-reducible compounds can also be put to beneficial use; this is, for example, the case of methylene blue.

According to one preferred embodiment of the invention, the replication of said predetermined target nucleotide sequence and the formation of replicated target nucleotide sequences in the form of nucleic acid double strands are caused. Thus, said activatable amplification means are of PCR type.

According to a second aspect, the present invention proposes an assembly for electrochemically identifying target nucleotide sequences. Said assembly comprises means for receiving a biological sample that may contain a predetermined target nucleotide sequence and activatable amplification means comprising free nucleotides in order to cause the replication of said predetermined target nucleotide sequence and the formation of replicated target nucleotide sequences. In addition, the assembly includes an oxido-reducible compound capable of reacting with respect to said nucleotides, said oxido-reducible compound being brought into contact with said biological sample. Activation means make it possible to activate said activatable amplification means, and means make it possible to apply an electric field to said sample in such a way as to activate said oxido-reducible compound, while measuring means make it possible to measure the electric current representative of the electrical activity of said oxido-reducible compound, which passes through said sample. Finally, determining means make it possible to determine the presence of said predetermined target nucleotide sequence if the electric current decreases. According to the invention, said oxido-reducible compound is chosen from compounds capable of intercalating, during the replication, between the nucleotides forming said replicated target sequences, i.e. in the double strands of the replicated target nucleotide sequence, said replicated target sequences causing the inhibition of the electrochemical activity of said intercalated oxido-reducible compound, by virtue of which the electric current decreases.

In addition, and according to one advantageous embodiment, the identification assembly also comprises means for supplying said sample with thermal energy in such a way as to cause the release of said intercalated oxido-reducible compound, and means for applying an electric field to said sample, by virtue of electrodes brought into contact with the sample, in such a way as to simultaneously record, as a function of the temperature, the variations in electric current which passes through said sample, and also means for determining the amount of thermal energy corresponding to the maximum variations in the electric current which are recorded, in order to check the presence of said predetermined target nucleotide sequence. These means determine, on the basis of the maximum variation in the electric current recorded, the dissociation temperature (Tm) characteristic of the presence of target nucleotide sequence to be detected. The abovementioned electrochemical identification assembly which makes it possible to implement the method in accordance with the invention will be explained in greater detail in the description which follows. In particular, the activating means, which are advantageously capable of activating said activatable amplification means according to successive amplification cycles in order to duplicate said replicated target sequence at each amplification cycle will be described. In addition, the identification assembly according to the invention comprises recording means for recording the number of amplification cycles corresponding to the decrease in the electric current in such a way as to determine the concentration of said target nucleotide sequence in said sample.

BRIEF DESCRIPTION OF THE DRAWINGS

In addition, other particularities and advantages of the invention will emerge on reading the description, provided hereinafter, of a particular embodiment of the invention, given by way of nonlimiting indication, with reference to the appended drawings in which.

DESCRIPTION OF PREFERRED EMBODIMENTS

Figure 1:
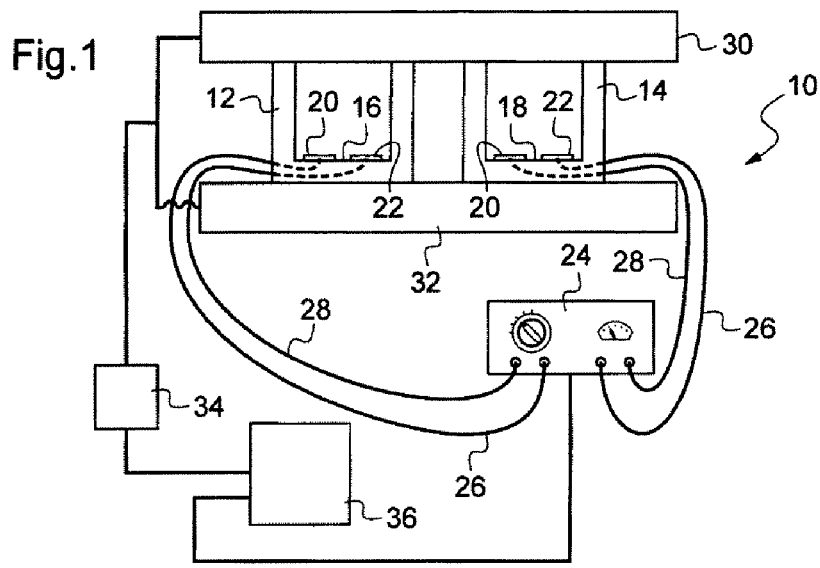
FIG. 1 is a diagrammatic view of an electrochemical identification assembly in accordance with the invention.

The electrochemical identification method in accordance with the invention requires the use of an electrochemical identification assembly comprising, on the one hand, controlling and measuring means, which will firstly be described, and, on the other hand, specific biological and chemical constituents. Thus, an electrochemical identification apparatus 10 in accordance with the invention has been represented diagrammatically in FIG. 1. This FIG. 1 shows two microcuvettes 12, 14, suitable for receiving, inside, a biological sample of which the characteristics will be defined hereinafter. These microcuvettes 12, 14, already known according to the prior art, have, respectively, a bottom 16, 18, on which are present an electrode 20, a counter electrode 22 and a nonrepresented reference electrode, obtained, for example, by screenprinting and respectively connected to a potentiostat 24, the first two by means of conducting wires 26, 28. In addition, they are sandwiched between a Pelletier-effect module 32 which supports them and a heating cap 30, which are connected to a generator 34. As will be explained hereinafter, the Pelletier-effect module 32 makes it possible to give up a given amount of thermal energy to the content of the microcuvettes 12, 14. Moreover, the generator 34 and the potentiostat 24 are controlled by a microcomputer 36, which contains a computer program and recording means.

Thus, these microcuvettes 12, 14 constitute receiving means capable of receiving a biological sample, which biological sample may include a nucleic acid sequence, in particular DNA, which contains a predetermined target nucleotide sequence intended to be detected. In addition, the Pelletier-effect module 32, and the generator 34 capable of being controlled by means of the microcomputer 36, constitute a first part of activatable amplification means, the second part consisting of the biological material and the chemical compounds.

Figure 2A:
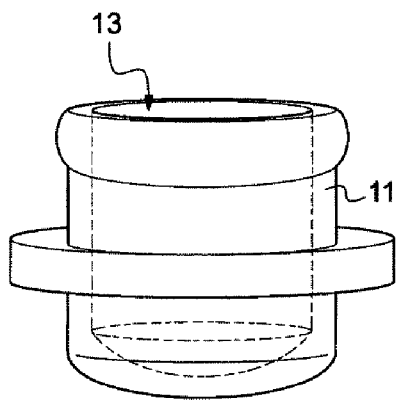
FIGS. 2A to 2C are diagrammatic views of an element of the identification assembly represented in FIG. 1, according to one variant embodiment.
Figure 2B:
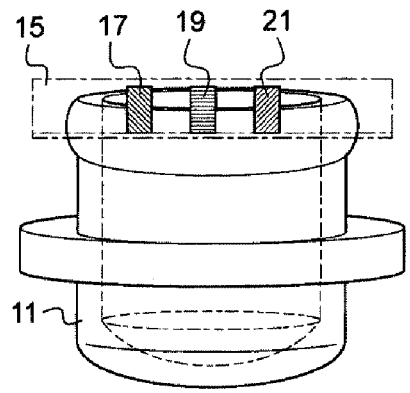
Figure 2C:
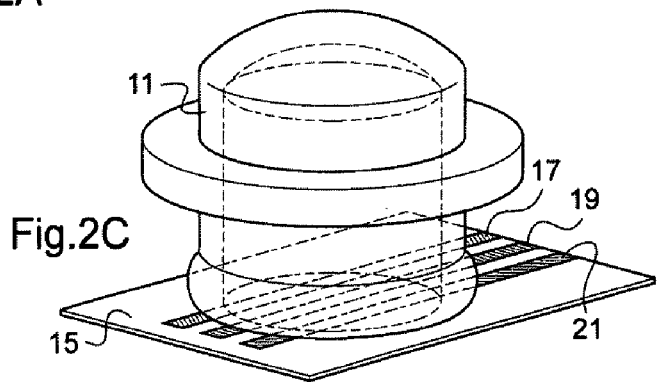

Of course, other well-known receiving means, which are not represented, comprise a tube into the base of which the biological sample is placed. The tube is then equipped with electrodes capable of immersing in this biological sample and of being connected to the potentiostat. The tube is then intended to be installed in a thermocycler in order to bring the biological samples to predetermined temperatures and according to predefined time cycles. Yet other receiving means, illustrated in FIGS. 2A to 2C, make it possible to receive the biological samples. They comprise a container 11 of small dimensions, for example a tube cap, represented in FIG. 2A, which can contain from 1 µl to 1 ml for example, and the upper part 13 of which is open. It is capable of receiving the reaction mixture. It is then hermetically sealed by means of a film 15 on which three unconnected electrodes 17, 19, 21 have been screen-printed. The electrodes 17, 19, 21 are oriented toward the inside of the container 11 and they emerge therefrom at the juncture between the edge of the container and the film 15. Next, the container 11 provided with its film 15 is then turned over so as to be brought to bear against a Pelletier-effect module and, consequently, the reaction mixture initially in the bottom of the container 11 comes into contact with the electrodes 17, 19, 21, which bathe in said mixture.

The amplification method used here is the "PCR" method. Thus, by means of the Pelletier-effect module 32, the inside of the microcuvettes 12, 14 is capable of being brought to predetermined temperatures for periods of time which are also predetermined and according to the following protocol: the protocol begins with a first stage of 1 to 15 minutes according to the type of polymerase, in which the inside of the microcuvettes 12, 14 is brought to a temperature of 94-95° C.; next, a certain number of consecutive cycles of temperature according to the amplification required for the detection of the replicated target nucleotide sequence, conventionally between 10 and 50 cycles, are applied to the microcuvettes 12, 14, according to four successive stages per cycle, a first "denaturation" stage conventionally of 1 to 60 seconds at a temperature of 94-95° C.; a second "primer annealing" stage, conventionally of 1 to 60 seconds at a temperature between 40° C. and 72° C., characteristic of the primers specific for the predetermined target nucleotide sequence; a third "elongation" stage, conventionally of 1 to 60 seconds at 72° C., and a final stage of a few seconds at a temperature of between 40° C. and 95° C., which is determined by the time required for the electrochemical measurement. The conditions for implementing this first amplification-means part will be described hereinafter, after having described the second part comprising, in particular, the biological material and the chemical compounds.

Since one of the objects of the invention is to amplify a nucleic acid sequence by replication and to electrochemically measure its presence in the medium during the amplification process, it is advisable first of all to have biological material enabling this amplification. In order to carry out the PCR technique, it is advisable to bring into contact with the nucleic acid to be amplified a polymerase enzyme, a pair of primers and the four free nucleotides: dGTP, dATP, dTTP and dCTP which constitute DNA, respectively deoxyguanosine triphosphate, deoxyadenosine triphosphate, deoxythymidine triphosphate and deoxycytosine triphosphate. Analogs of bases of the deoxyribonucleotide triphosphate type, such as deoxy-deazaguanosine triphosphate, can also be used.

Thus, according to a first example of application, in addition to a biological sample to be tested and in fact an extract of cytomegalovirus DNA containing a target nucleic acid sequence of 283 base pairs, the DNA polymerase, i.e. the enzyme, the primers and the four types of nucleotides are introduced into one of the microcuvettes 12, the whole forming a reaction mixture which is of course liquid and buffered. In addition, in order to be able to measure the intensity of an electric signal, an oxido-reducible compound is added to the reaction mixture, said oxido-reducible compound being, in the case in point, the osmium complex: bis(2,2'-bipyridine) dipyrido[3,2-a:2',3'-c]phenazine osmium (II) the CAS number of which may be 3555395-37-8, which in our case is denoted [Os$^{II}$(bpy)$_2$DPPZ]$^{2+}$ and which is of formula I:

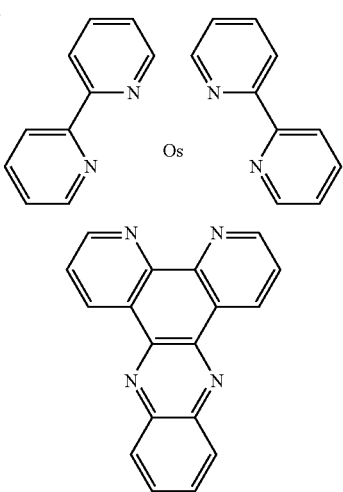

Formula 1

Other oxido-reducible compounds can be envisioned, and in particular with ruthenium in place of the osmium. Other ligands may also be used. The advantage of the dipyridophenazine ligand lies in its ability to intercalate between the nucleotides forming the target nucleic acid sequences. As other ligands that can be envisioned, mention will, for example, be made of DPPX: 7,8-(dimethyl)dipyrido[3,2-a:2, 3-c]phenazine; PTDB: 3-(pyridin-2-yl)-5,6-diphenyl-as-triazine; or DPT: 3-(pyrazin-2-yl)-as-triazino[5,6-f] phenanthrene; or else ligands which have a quinone function, such as PHI: phenanthrenequinone diimine.

DNA-intercalating and oxido-reducible organic compounds may also be used in the method which is the subject of the invention. Mention will be made, for example, of ethidium bromide, acridine and derivatives thereof, acridone derivatives or else phenazine derivatives.

For experimental and control purposes, the identical elements mentioned above, except for the biological sample to be tested, are introduced into the other microcuvette 14. According to one exemplary embodiment, the concentrations of the various elements introduced into the microcuvettes 12, 14 are listed in table I below.

TABLE 1

|  | Microcuvette 12 | Microcuvette 14 |
|---|---|---|
| Left primers | 250 nM |  |
| Right primers | 250 nM |  |
| Free nucleotides: dNTPs | 200 µM |  |
| PCR buffer | 1 x |  |
| Enzyme: Hot Star Taq | 0.1 U/µL |  |
| [Os(bpy)$_2$-dppz] | 0.5 µM |  |
| Extract of cytomegalovirus DNA of 283 base pairs | 100 000 copies | 0 copies |

Thus, the reaction mixture contained in the two microcuvettes 12, 14 is, by means of the Pelletier-effect module 32, controlled by the microcomputer 36, brought to various temperatures for predetermined periods of time. After the preliminary stage in which the reaction mixture is brought once to a temperature of 95° C. for 15 minutes, the reaction mixture is brought, on the first stage, to a temperature of 94° C. for 30 seconds so as to dehybridize the target nucleic acid sequences, i.e. to dissociate the two complementary strands of the target nucleic acid sequences; next, it is brought, on the second stage, to 53° C. for 60 seconds in order for the respective primers to hybridize to the dissociated DNA strands; then, it is brought, on the third stage, to 72° C. for 60 seconds in order to allow the polymerases to synthesize a complementary strand and to thus form the amplicon and the replicated target sequence that it includes. Finally, the reaction mixture is brought to a temperature of 85° C., on a fourth stage, for 10 seconds during which the use of the potentiostat 24 is controlled by means of the microcomputer 36.

According to the first example of application defined above, on the predefined fourth stage and during the period of 10 seconds, the intensity/potential curve in a region of potential framing the standard potential of the oxido-reducible compound is recorded by square wave voltammetry by means of the potentiostat 24. A potential difference is thus applied between the electrode 20 and the counter electrode 22 and this potential difference is varied according to a square wave profile. In parallel, the electric current which passes through these electrodes is measured and an intensity/potential curve is obtained in the form of a peak of which the maximum current value, after subtraction of a base line, is representative of the concentration of nonintercalated oxido-reducible compound present in solution.

Figure 3A:
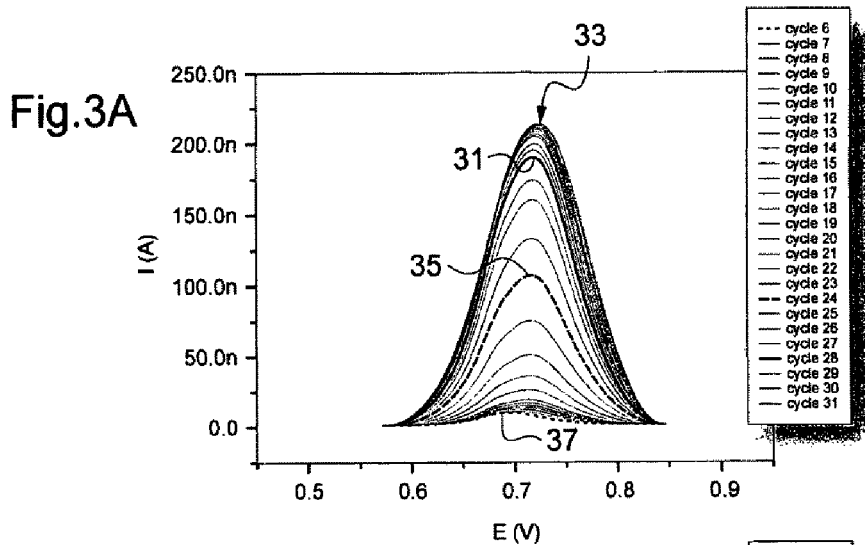
FIGS. 3A and 3B are intensity/potential diagrams obtained by means of the identification assembly represented in FIG. 1.
Figure 3B:
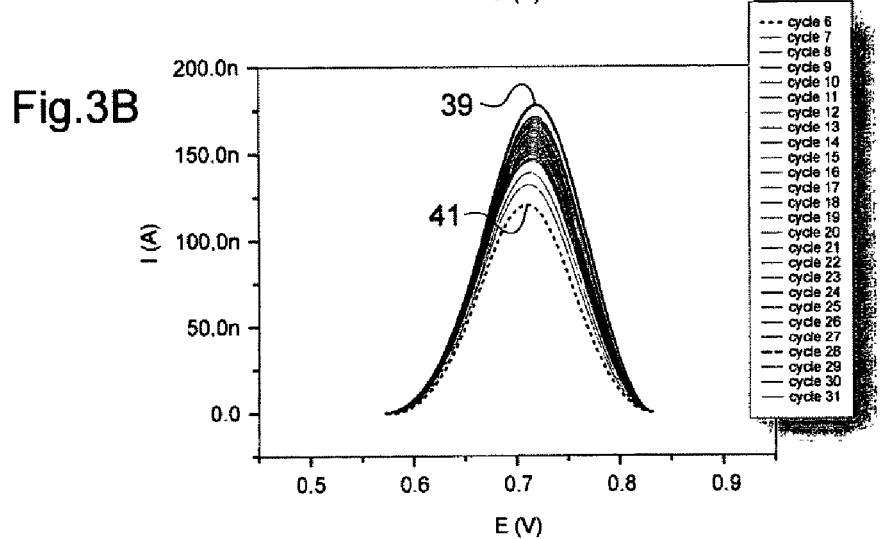
Figure 3C:
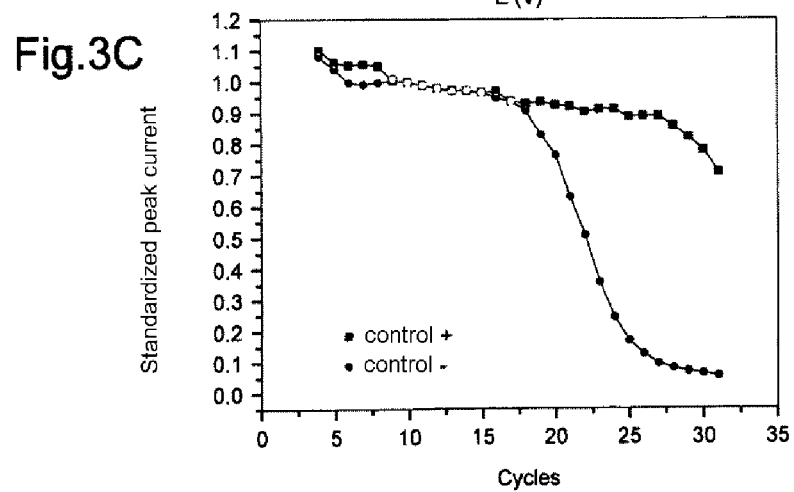
FIG. 3C is a view of a diagram obtained by deduction of the diagrams represented in FIGS. 3A and 3B.

Reference will thus be made to FIGS. 3A to 3B first of all, and then to FIG. 3C. Specifically, 31 replication cycles were applied to the biological samples contained in the microcuvettes 12, 14. FIG. 3A illustrates the change in the intensity/potential curves as a function of the cycles, for the biological samples including the target nucleotide sequence being sought, while FIG. 3B represents the change in the intensity/potential curves as a function of the cycles, for the reaction mixture devoid of target sequence. In FIG. 3A, the summit 33 of the curve decreases significantly, i.e. the consumption of oxido-reducible compound is appreciable, starting from the $18^{th}$ cycle 31 and reaches the mid-height 35 at the $22^{nd}$ cycle. At the $31^{st}$ cycle, the curve 37 becomes virtually flat and its summit reaches an intensity value which is 5% less than those of the first cycles. Thus, the oxido-reducible compound has been incorporated into the double-stranded DNA molecules formed. This implies that the target nucleotide sequence being sought was indeed present in the biological samples.

Conversely, in FIG. 3B, the extreme 39 of the curve remains at a substantially constant value until the $31^{st}$ cycle, in comparison with the previous curve, since, in these samples, the target nucleotide sequence being sought is not present. Nevertheless, it decreases slightly in particular owing to the formation of primer dimers in the reaction mixture.

Thus, the presence of a target nucleotide sequence being sought is rapidly detected in any biological sample by means of the method described above.

It will be observed that the peak current value is standardized, by dividing it by the mean value corrected for the drift of the peak currents obtained during the first amplification cycles, i.e. when the amount of replicated target nucleotide sequence is not yet sufficient to cause the peak current measured to drop significantly, for example at the $5^{th}$ cycle.

Reference will be made to FIG. 3C illustrating the curves taken from the two series of curves mentioned above and showing the value of the peak current thus standardized as a function of the number of cycles carried out, for the two microcuvettes 12, 14 comprising, respectively, the biological sample to be tested and the biological material intended for the replication and also the oxido-reducible compound, and, in the other, solely the biological material with the oxido-reducible compound.

Thus, it is observed that, up to the $25^{th}$ cycle, the value of the current which passes through the reaction mixtures of the two microcuvettes 12, 14 is approximately parallel and relatively constant. On the other hand, between the $25^{th}$ cycle and beyond the $30^{th}$ cycle, it is observed that the value of the electric current which passes through the microcuvette 12, which includes the biological sample to be tested, drops abruptly in comparison with the electric current which passes through the other microcuvette 14, which is itself devoid of the predetermined target nucleic acid sequence. This abrupt and exponential drop in the electric current, according to an $\epsilon^c$ function, c being the number of cycles and $\epsilon$ the intensity of amplification close to 2, attests to the amplification of the predetermined target nucleotide sequence, for which the primers were specific, and to the resulting production of replicated target sequences. Specifically, the production of replicated target nucleic acid sequence molecules then causes inactivation of the abovementioned oxido-reducible compound, via the intercalation of said compound into the formed double strand of the replicated nucleic acid sequence. The oxido-reducible compound, which is thus inactive, can no longer exchange charges with the surface of the electrodes 20, 22 and, consequently, can no longer be detected electrochemically. This results in a drop in the electrical signal, which then reveals the formation of the predetermined target nucleotide sequence by means of the specific primers, in the biological sample explored.

The current is recorded at a temperature above the "dissociation" temperature of the primer dimers and/or other DNA sequences not specifically amplified. The choice of the temperature at which the measurement is carried out is an essential parameter for distinguishing between a false-positive and a true-positive sample.

Figure 4:
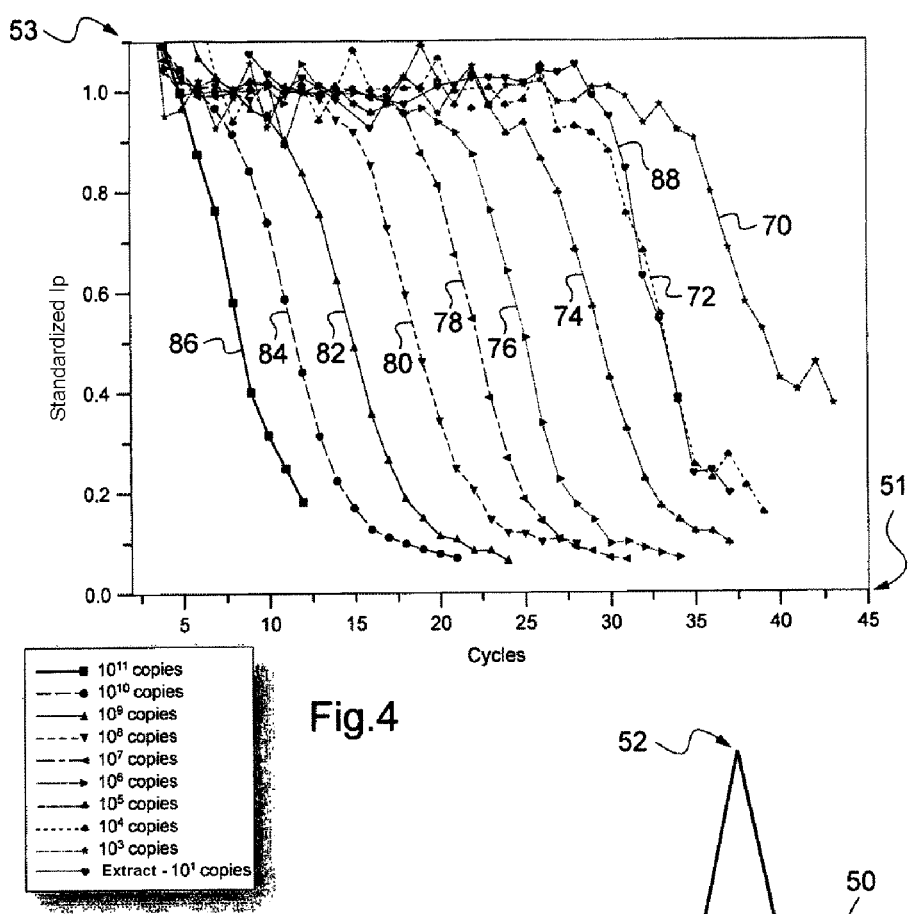
FIG. 4 is a view of a diagram of a type analogous to that of FIG. 3C.

Moreover, reference will presently be made to the graph illustrated in FIG. 4, in order to describe, according to a second example of application, the principle of the quantification of a predetermined target nucleotide sequence in a given sample.

Along the x-axis 51 of the graph are the numbers of cycles of replication of the amplification means, and along the y-axis 53 are the standardized values of the maximum current, recorded at each cycle according to the embodiment illustrated in FIG. 3A.

On this graph of FIG. 4, nine calibration curves are represented from right to left, 70, 72, 74, 76, 78, 80, 82, 84 and 86, and they show intermediate portions which are approximately parallel to one another and in a direction close to vertical. These curves correspond, respectively, to the various plots obtained by starting from a biological sample comprising $10^3$ copies of the target sequence contained in the cytomegalovirus genome for the first of the nine curves, which is curve 70, and $10^{11}$ for the ninth curve, which is curve 86. From the first curve 70 to the last curve 86, the number of copies is, for each subsequent curve, multiplied by ten.

Thus, it is noted that, the greater the amount of predetermined target nucleotide sequence contained by the biological sample, the earlier the electric current which passes through the electrode decreases as a function of the number of cycles. This is because the more nucleic acids incorporating the predetermined target sequence the sample contains at the start, the lower the number of cycles necessary for producing, by replication, the same amount of predetermined target nucleotide sequences, and, consequently, the earlier the decrease in the current via the intercalation of the oxido-reducible compound into the double strands of the replicated target nucleotide sequences. In that way, it is understood that it is possible to measure the amount of nucleic acids incorporating the target sequence by determining the number of cycles starting from which the amount of current which passes through the sample dips. In addition, the first curve 70 on FIG. 4 shows that the presence of the target sequence is still detectable when only 1000 copies of said target sequence are initially present in the sample.

An extract initially with a concentration of predetermined target nucleic acid sequence was thus tested, and its curve 88 appears as a broken line along the second calibration curve 72 corresponding to $10^4$ copies of the target sequence.

Thus, the method according to the invention applied to a biological sample that may contain a predetermined target nucleotide sequence makes it possible not only, by means of implementing a method of amplification and of an electrochemical measurement of a double-stranded-DNA-intercalating oxido-reducible agent, to reveal the presence or absence of the predetermined target nucleotide sequence, but also to quantify it with a signal amplitude, a reproducibility and a sensitivity that are improved in comparison with the other electrochemical methods according to the prior art. This method takes advantage of the oxido-reducible properties of an agent which intercalates nucleic acid sequences forming a double strand, which is in no way used in the conventional amplification methods, for revealing the presence of a target nucleic acid sequence.

With the aim of refining the detection method, in particular in terms of specificity of identification of the amplified target sequence, the gradual dehybridization of all the replicated target sequences is brought about, at the end of the amplification, by means of a gradual increase in temperature of the sample, so as to release the intercalated oxido-reducible compound. Since this oxido-reducible compound then again becomes electrochemically detectable, it is once more capable of supplying an electrical signal to the electrodes, representative of the amount of oxido-reducible compound released and, consequently, of the nature and therefore of the length of the predetermined target nucleotide sequence.

This dehybridization is carried out by gradually bringing, according to a suitable temperature ramp, the DNA molecules from a temperature where all the double strands are paired, i.e. around 40° C., to a temperature where all the double strands are dissociated, i.e. around 98° C., and the abovementioned Pelletier-effect module 32 constitutes preferred means for this. The latter in fact make it possible to supply the reaction mixture contained in the two microcuvettes 12, 14, represented in FIG. 1, with thermal energy so as to cause the dehybridization of the replicated target nucleotide sequences and, consequently, the release of said intercalated oxido-reducible compound. In addition, by virtue of the potentiostat 24 and by means of the microcomputer 36, a potential difference is then applied between the electrode 20 and the counter electrode 22 and this potential difference is varied according to the abovementioned square wave profile. The electric current which passes through these electrodes is measured and in that way a peak current is determined.

Thus, by virtue of the Pelletier-effect module 32, the temperature of the reaction mixtures is incremented, for example degree by degree, between 70° C. and 95° C. In parallel, as soon as the temperature of the reaction mixtures increases by 1° C., a potential difference is applied between the electrodes 20, 22 and the current which passes through them is measured according to the abovementioned voltammetry method.

Figure 5A:
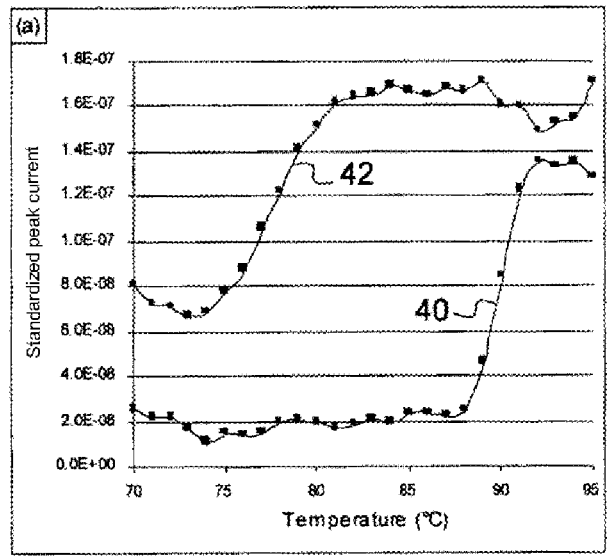
FIG. 5A illustrates an intensity/temperature diagram obtained by means of the identification assembly represented in FIG. 1 and in a first step.

Reference will now be made to FIG. 5A showing, according to a third example of application, a diagram of the peak current then obtained as a function of the temperature, for the two microcuvettes 12, 14, one including the reaction mixture with the target nucleotide sequence being sought, the other the reaction mixture without this target sequence.

The lower curve 40 thus obtained corresponds to the reaction mixture including the target nucleotide sequence and, consequently, a plurality of replicated target nucleotide sequences. Thus, it is observed that the increase in the temperature of the reaction mixture, between 70° C. and 88° C., produces no effect on the DNA molecules which include the target nucleotide sequences. On the other hand, between 88° C. and 92° C., the peak current is multiplied by seven. This peak current is then directly proportional to the amount of oxido-reducible compound released and, consequently, the nature and therefore the length of the predetermined target nucleic acid sequence, which in this case is 283 base pairs.

It will be observed with the upper curve 42, corresponding to the reaction mixture devoid of predetermined target nucleic acid sequence, that the electrical signal measured doubles between 70° C. and 85° C. This is the result of the intercalation in the primer dimers and other double strands synthesized nonspecifically and which are smaller than the predetermined target nucleic acid sequence.

Bringing to light the target nucleotide sequence being sought is then more probative if each point of the curves represented in FIG. 5A is transposed to the value of the derivative at this point. In that way, the fusion curves represented in FIG. 5B are obtained.

Thus, the lower curve 40 corresponding to the reaction mixture including the target sequence is transformed into a typical curve 44 having a significant peak 46 at the temperature of 90° C. Of course, this significant peak 46 corresponds to the abrupt variation in peak current observed in FIG. 5A for the lower curve 40. This significant peak 46 is representative of the nature and therefore of the length of the predetermined target sequence through the temperature at which it appears. Specifically, the more the target sequence being sought is mainly long, the greater the amount of oxido-reducible compound included in the amplicons, quite obviously for an equivalent amount of amplicons. Thus, in order to release the molecules of the oxido-reducible compound, it will be necessary to provide a greater amount of thermal energy in order to dehybridize the double strand formed by the predetermined target sequence. Consequently, the temperature at which this dehybridization will occur will be all the higher. Furthermore, since the amount of molecules of oxido-reducible compound included in the amplicons is greater, once it is released, the electrical signal recorded will also be accordingly greater.

Consequently, the more the target nucleotide sequence being sought is mainly long in nature, the higher the significant peak 46 and the more it is shifted toward a high temperature.

Figure 5B:
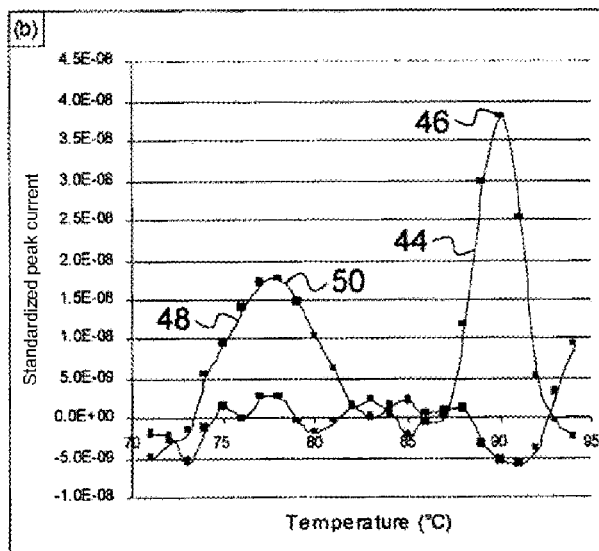
FIG. 5B illustrates a diagram obtained in a second step by transposition of the diagram illustrated in FIG. 5A.

On the other hand, as regards the upper curve 42 represented on FIG. 5A, its transformation into a derived curve 48 represented in FIG. 5B reveals a broad peak 50 at a temperature between 75° C. and 80° C. This broad peak 50 corresponds quite simply to the dehybridization of the primer dimers and other double strands synthesized nonspecifically and smaller than the predetermined target nucleic acid sequence, which then causes the release of the oxido-reducible compound. It will be observed that this broad peak 50 appears in a temperature range below that of the significant peak 46 and that it is more diffuse.

According to a fourth example of application, it is shown that it is possible to detect the presence of at least two distinct target nucleotide sequences, in the same biological sample, by means of the identification method in accordance with the invention.

To do this, the identification assembly represented in FIG. 1 is quite obviously used, and three series of measurements are carried out in accordance with the examples of application described above. It is in this case a question of showing that it is possible to identify, in the same biological sample, the presence of a bacterium, *Achromobacter xylosoxidans*, of which the size of the target nucleotide sequence is 100 base pairs, and the human cytomegalovirus, previously used, of which the size of the target nucleotide sequence is 283 base pairs. A first series of measurements corresponds to the human cytomegalovirus and is carried out under the same conditions as those described above. A second series of measurements corresponds precisely to the bacterium *Achromobacter xylosoxidans* and, consequently, the amplification material includes the primers specific for the corresponding target sequence. In addition, a third series of measurements corresponds to the mixture of the human cytomegalovirus and the bacterium *Achromobacter xylosoxidans*, and, consequently, the amplification material in this case includes the corresponding two specific primers in the mixture.

The fusion curves for the three series of measurements are then produced in accordance with the third example of application.

Figure 6:
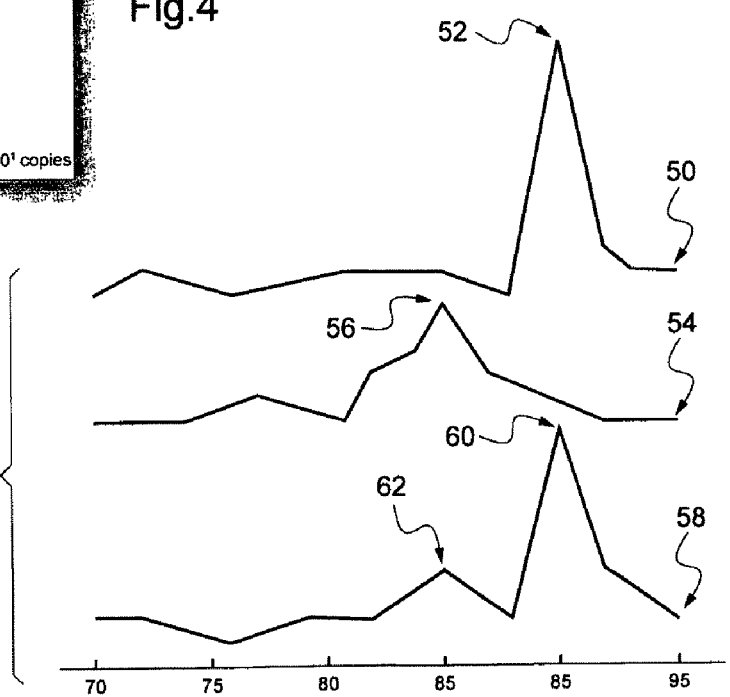
FIG. 6 illustrates a diagram of the type represented in FIG. 5B, in a particular application.

The three curves then obtained have been represented in FIG. 6 and, for greater clarity, they have been shifted with respect to one another along the y-axis. Thus, a first curve 50, relating to the human cyto-megalovirus, and which corresponds to the typical curve 44 illustrated in FIG. 5B, is found in this FIG. 6.

A significant first peak 52 is thus found for a temperature value equivalent to 90° C. Moreover, as regards the bacterium *Achromobacter xylosoxidans*, the fusion curve 54 corresponding to the second series of measurements is characterized by a second significant peak 56 for a temperature value around 85° C.

In addition, finally, the third series of measurements results in a third curve 58 exhibiting a third significant peak 60 and a fourth significant peak 62, for temperature values equivalent to 90° C. and to 85° C., respectively. These values correspond exactly to those of the bacterium alone and of the human cytomegalovirus alone.

The possibility of detecting a plurality of target nucleotide sequences in the same biological sample by means of the identification method in accordance with the invention is thus shown by means of this fourth example of application.

According to one embodiment of the invention which is particularly advantageous, and not represented here, but in accordance with the invention, it is envisioned to be able to amplify a target sequence possibly having certain differences in its sequence and to identify the presence or absence of these differences by means of a fusion curve, as defined above.

What is claimed is:

1. A method for electrochemically identifying a predetermined target nucleotide sequence in a biological sample by real-time detection, comprising:
    providing the biological sample;
    providing material for activatable amplification comprising free nucleotides used for replication of the predetermined target nucleotide sequence and for the formation of replicated target nucleotide sequences;
    bringing an oxido-reducible compound capable of intercalating between the nucleotides forming the replicated target sequences, and which does not oxidize the nucleotide bases of the free nucleotides in the biological sample, into contact with the biological sample and the provided material for activatable amplification, the oxido-reducible compound comprising a metal and at least one ligand, the metal being selected from the group consisting of osmium and ruthenium, and the at least one ligand being selected from the group consisting of dipyrido[3,2-a:2',3'-c]phenazine, 7,8-(dimethyl)dipyrido[3,2-a:2,3-c]phenazine (DPPZ), 3-(pyridin-2-yl)-5,6-diphenyl-as-triazine (PTDB), 3-(pyrazin-2-yl)-as-triazino[5,6-f]phenanthrene (DPT), and phenanthrenequinone diimine (PHI);
    activating the material for activatable amplification, in a series of amplification cycles, to successively increase a quantity of double stranded replicated target sequences dependent on a quantity of the predetermined target nucleotide sequence in the biological sample, wherein a portion of the oxido-reducible compound intercalates between the nucleotides forming the replicated target sequences after formation, the intercalated portion of the oxido-reducible compound having inhibited electrochemical activity with respect to a non-intercalated portion;
    applying an electric field during each cycle of amplification while the portion of the oxido-reducible compound intercalates between the nucleotides forming the replicated target sequences, to selectively measuring an electric current representative of the electrochemical activity of the portion of the oxido-reducible compound that is non-intercalated, distinguished from the intercalated portion of the oxido-reducible compound; and
    quantitatively determining the presence of the predetermined target nucleotide sequence based on the measurement of the electric current during a time when the portion of the oxido-reducible compound is intercalated with the double stranded replicated target sequences,
    wherein the replication of the predetermined target nucleotide sequence by activating the material for activatable amplification causes a reduction in the portion of the intercalated oxido-reducible compound which is not intercalated, resulting in a quantitative decrease in the electric current as the fraction of intercalated oxido-reducible compound increases.

2. The identification method as claimed in claim 1, wherein the double stranded replicated target sequences are separated into single stranded target sequences, and the single stranded target sequences are duplicated, forming the increased quantity of double stranded replicated target sequences, with an increased quantity of intercalated oxido-reducible compound.

3. The identification method as claimed in claim 2, wherein the number of amplification cycles corresponding to the decrease in the electric current is recorded in order to determine the concentration of the predetermined target nucleotide sequence in the biological sample.

4. The identification method as claimed in claim 1, further comprising:
    the sample is supplied with thermal energy in order to cause the release of the intercalated oxido-reducible compound, and an electric field is applied to the biological sample in order to simultaneously record the variations in electric current which passes through the biological sample; and
    the amount of thermal energy Q corresponding to the maximum variations in the electric current which are recorded is determined in order to identify the nature of the predetermined target nucleotide sequence.

5. The identification method as claimed in claim 4, wherein the biological sample is supplied with thermal energy so as to cause a gradual increase in the temperature of the biological sample.

6. The identification method as claimed in claim 5, wherein the gradual increase in the temperature is caused between 40° C. and 98° C.

7. The identification method as claimed in claim 1, wherein the electric current representative of the electrochemical activity of the oxido-reducible compound is measured at a predetermined temperature of the biological sample.

8. The identification method as claimed in claim 5, wherein the gradually increased temperature is lower than the temperature of the biological sample corresponding to the amount of thermal energy Q.

9. The identification method as claimed in claim 1, wherein voltammetry is used for measuring the electric current.

10. The identification method as claimed in claim 9, wherein square wave voltammetry is used for measuring the electric current.

11. The identification method as claimed in claim 1, wherein the oxido-reducible compound is a complex of a metal selected from the group consisting of osmium and ruthenium.

12. The identification method as claimed in claim 11, wherein the oxido-reducible compound has at least one nucleic-acid-sequence-intercalating ligand.

13. The identification method as claimed in claim 11, wherein the oxido-reducible compound has a dipyridophenazine ligand.

14. The identification method as claimed in claim 1, wherein said activating is conducted in a series of heating cycles, to cause successive selective amplification of the predetermined target nucleotide sequence.

15. The identification method as claimed in claim 1, wherein the activatable amplification material is of a PCR type.

16. A method for electrochemically determining in real-time a quantity of a target nucleotide sequence in a biological sample that may contain the target nucleotide sequence, comprising:
    combining a mixture of the biological sample, an activatable amplification material comprising free nucleotides adapted for replication of the predetermined target nucleotide sequence and for the formation of replicated target nucleotide sequences, and an oxido-reducible compound which intercalates between the nucleotides forming double stranded nucleic acids, the oxido-reducible compound comprising a metal and at least one ligand, the metal being selected from the group consisting of osmium and ruthenium, and the at least one ligand being selected from the group consisting of dipyrido[3,2-a:2',3'-c]phenazine, 7,8-(dimethyl)dipyrido[3,2-a:2,3-c]phenazine (DPPZ), 3-(pyridin-2-yl)-5,6-diphenyl-as-triazine (PTDB), 3-(pyrazin-2-yl)-as-triazino[5,6-f]phenanthrene (DPT), and phenanthrenequinone diimine (PHI), and having a first electrochemical activity in the mixture in a non-intercalated state, and a second electrochemical activity in the mixture in an intercalated state, the second electrochemical activity being inhibited with respect to the first electrochemical activity, wherein a measurable electrochemical activity of the mixture is dependent on respective proportions of the oxido-reducible compound being non-intercalated and having the first electrochemical activity and the oxido-reducible compound being intercalated between nucleotides of double stranded nucleic acids and having the second electrochemical activity;
    activating the activatable amplification material according to successive amplification cycles, to selectively form an amplified quantity of double stranded replicated target nucleotide sequences if the target nucleotide sequence is present in the biological sample, wherein a portion of the oxido-reducible compound intercalates within the amplified quantity of double stranded replicated target nucleotide sequences;
    applying an electric field to the mixture during a portion of a plurality of the successive amplification cycles during which the oxido-redicible compound is intercalated, in order to activate the oxido-reducible compound and measuring the electric current representative of the electrochemical activity of the oxido-reducible compound, dependent on the proportions of the oxido-reducible compound having the first electrochemical activity and having the second electrochemical activity, which passes through said combined the mixture; and
    quantitatively determining the presence of the predetermined target nucleotide sequence based on the measured electric current during a time when a portion of the oxido-reducible compound is intercalated with double stranded replicated target sequences,
    wherein replication of target sequences to form an increased quantity of double stranded replicated target sequences increases an inhibition of electrochemical activity by the intercalated oxido-reducible compound, resulting in a quantitative decrease in the measured electric current as the fraction of intercalated oxido-reducible compound increases.

17. A method for electrochemically identifying target nucleotide sequences in a real-time process, comprising:
    providing a biological sample that may contain a predetermined target nucleotide sequence;
    providing material for activatable amplification comprising free nucleotides used for replication of said predetermined target nucleotide sequence and for the formation of double stranded replicated target nucleotide sequences;
    bringing an oxido-reducible compound capable of intercalating between the nucleotides forming said double stranded replicated target nucleotide sequences and reversibly oxidizing in response to an electric field into contact with said biological sample substantially without oxidizing the nucleotide bases of the free nucleotides in the biological sample, the oxido-reducible compound comprising a metal and at least one ligand, the metal being selected from the group consisting of osmium and ruthenium, and the at least one ligand being selected from the group consisting of dipyrido[3,2-a:2',3'-c]phenazine, 7,8-(dimethyl)dipyrido[3,2-a:2,3-c]phenazine (DPPZ), 3-(pyridin-2-yl)-5,6-diphenyl-as-triazine (PTDB), 3-(pyrazin-2-yl)-as-triazino[5,6-f]phenanthrene (DPT), and phenanthrenequinone diimine (PHI);
    activating said material for activatable amplification according to successive amplification cycles, to replicate said predetermined target nucleotide sequence to form an increased quantity of double stranded replicated target nucleotide sequences, wherein a fraction of said oxido-reducible compound intercalated with said double stranded replicated target nucleotide sequences increases in response to said replication, and a fraction of said oxido-reducible compound not intercalated with said double stranded replicated target nucleotide sequences is reduced in response to said replication, if the predetermined target nucleotide sequence is present;
    applying an electric field to said oxido-reducible compound in contact with the biological sample during a plurality of the successive cycles, in order to activate said oxido-reducible compound during at least a time when a portion of the oxido-reducible compound is intercalated with said double stranded replicated target nucleotide sequences if the predetermined target nucleotide sequence is present, and measuring the electric current representative of the electrochemical activity of said oxido-reducible compound which passes through said oxido-reducible compound in contact with the biological sample, wherein an electrochemical activity of the intercalated fraction of the oxido-reducible compound is inhibited with respect to an electrochemical activity of a non-intercalated fraction, the measured electric current selectively corresponding to the non-intercalated fraction of the oxido-reducible compound, wherein said oxido-reducible compound is substantially not irreversibly consumed; and
    quantitatively determining the presence of the predetermined target nucleotide sequence based on a measurement of the electric current during at least the time when a portion of the oxido-reducible compound is intercalated with said double stranded replicated target nucleotide sequences,
    wherein the replication of target nucleotide sequences to form double stranded replicated target nucleotide sequences causes a decrease of electrochemical activity of the oxido-reducible compound in contact with the biological sample during the time when a portion of the oxido-reducible compound is intercalated with said double stranded replicated target nucleotide sequences, resulting in a quantitative decrease in the electric current as the fraction of intercalated oxido-reducible compound increases.

18. The method as claimed in claim 17, wherein each cycle of the successive amplification cycles comprises separating double stranded replicated target nucleotide sequences into single stranded target nucleotide sequences, and the single stranded target nucleotide sequences are duplicated, forming an increased quantity of double stranded replicated target nucleotide sequences, with an increased quantity of intercalated oxido-reducible compound.

* * * * *